(12) United States Patent
Meissner et al.

(10) Patent No.: US 7,569,581 B2
(45) Date of Patent: *Aug. 4, 2009

(54) ANTICHOLINERGICS WHICH MAY BE USED AS MEDICAMENTS AS WELL AS PROCESSES FOR PREPARING THEM

(75) Inventors: Helmut Meissner, Ingelheim (DE); Gerd Morschhaeuser, Ingelheim (DE); Michael Paul Pieper, Ingelheim (DE); Gerald Pohl, Biberach (DE); Richard Reichl, Gau-Algesheim (DE); Georg Speck, Ingelheim (DE); Rolf Banholzer, Stuttgart (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/117,163

(22) Filed: Apr. 28, 2005

(65) Prior Publication Data

US 2005/0197357 A1    Sep. 8, 2005

Related U.S. Application Data

(63) Continuation of application No. 10/684,994, filed on Oct. 14, 2003, now abandoned, which is a continuation of application No. 09/976,950, filed on Oct. 11, 2001, now Pat. No. 6,706,726.

(60) Provisional application No. 60/252,777, filed on Nov. 22, 2000.

(30) Foreign Application Priority Data

Oct. 14, 2000  (DE) ................. 100 50 994

(51) Int. Cl.
A01N 43/42 (2006.01)
A61K 31/44 (2006.01)

(52) U.S. Cl. ....................................... 514/304

(58) Field of Classification Search .................. 514/304
See application file for complete search history.

(56) References Cited

U.S. PATENT DOCUMENTS

| 2,782,199 A | 2/1957 | Cusic et al. |
|---|---|---|
| 2,824,106 A | 2/1958 | Zeile et al. |
| 2,872,452 A | 2/1959 | Zeile et al. |
| 2,893,996 A | 7/1959 | Rudner et al. |
| 2,927,925 A | 3/1960 | Zaugg et al. |
| 3,145,211 A | 8/1964 | Feldkamp et al. |
| 3,502,683 A | 3/1970 | Banholzer et al. |
| 3,505,337 A | 4/1970 | Zeile et al. |
| 3,583,996 A | 6/1971 | Banholzer et al. |
| 3,673,195 A | 6/1972 | Yoneda et al. |
| 3,808,263 A | 4/1974 | Yoneda et al. |
| 4,042,700 A | 8/1977 | Banholzer et al. |
| 4,411,902 A | 10/1983 | Bernareggi et al. |
| 4,558,054 A | 12/1985 | Bernareggi et al. |
| 4,608,377 A | 8/1986 | Banholzer et al. |
| 4,783,534 A | 11/1988 | Banholzer et al. |
| 4,855,422 A | 8/1989 | Grimminger et al. |
| 5,610,163 A | 3/1997 | Banholzer et al. |
| 5,654,314 A | 8/1997 | Banholzer et al. |
| 5,770,738 A | 6/1998 | Banholzer et al. |
| 5,952,505 A | 9/1999 | Banholzer et al. |
| 6,419,899 B1 | 7/2002 | Weil et al. |
| 6,486,321 B2 | 11/2002 | Banholzer et al. |
| 6,506,900 B1 | 1/2003 | Banholzer et al. |
| 6,852,728 B2 | 2/2005 | Meissner et al. |
| 2002/0133010 A1 | 9/2002 | Banholzer et al. |
| 2003/0199545 A1 | 10/2003 | Grauert |
| 2005/0197357 A1 | 9/2005 | Meissner et al. |

FOREIGN PATENT DOCUMENTS

| DE | 40 03 270 A1 | 8/1991 |
|---|---|---|
| FR | 21688881 | 9/1973 |
| FR | 2208649 | 6/1974 |
| WO | WO 92/16528 A | 10/1992 |
| WO | 02/32898 A2 | 4/2002 |

OTHER PUBLICATIONS

Chapman, The role of anticholinergic bronchodilators in adult asthma and chronic obstructive pulmonary disease, PMID: 2143551 (1990).*
Holgate, Anticholinergics in acute bronchial asthma, PMID: 2962072 (1987).*
Scapecchi et al., Bioorganic & Medicinal Chemistry, 1994, vol. 2, pp. 1061-1074.*
Chemical Abstract, 59, 1963, 5665 g-h, 5666a.
Chemical Abstract, 61, 1964, 9361 f-h.
Schultz, et al; "Zum Problem des Wirkungs-zentrums bei Tropylestern"; Pharmazeutische Zeitung Nr. 40, 5, Oktober 1972, 1455-1456.
CAS Registry No. 53949-94-3.
CAS Registry No. 41055-56-5.
CAS Registry No. 40797-30-6.

(Continued)

*Primary Examiner*—D. Margaret Seaman
*Assistant Examiner*—Niloofar Rahmani
(74) *Attorney, Agent, or Firm*—Michael P. Morris; Mary-Ellen M. Devlin; Wendy A. Petka

(57) ABSTRACT

The present invention relates to new anticholinergics of general formula 1

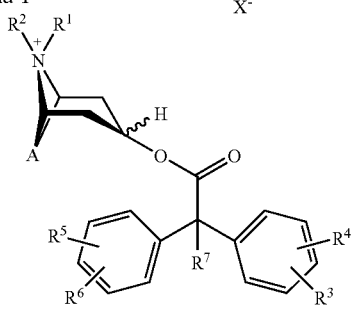

wherein A, $X^-$, and the groups $R^1$, $R^2$, $R^3$, $R^4$, $R^5$, $R^6$ and $R^7$ may have the meanings given in the claims and in the specification, processes for preparing them and their use as pharmaceutical compositions.

16 Claims, No Drawings

OTHER PUBLICATIONS

Chemical Abstract No. 118:81214 (1993).
Chemical Abstract No. 99:145 (1983).
Chemical Abstract No. 59:5665f-g (1963).
Chemical Abstract No. 54:15669d-e (1960).
Chemical Abstract No. 78:119197 (1973).
Chemical Abstract 122:204554, vol. 122, No. 17, Apr. 24, 1995.
Chemical Abstract 82:51342t, vol. 82, No. 9, Mar. 3, 1975.
Chemical Abstract 77:135027, vol. 77, No. 21, Nov. 20, 1972.
Chemical Abstract 128:252519, vol. 128, No. 21, May 25, 1998.
Chemical Abstract 126:292958, vol. 126, No. 22, Jun. 2, 1997.
Chemical Abstract 90:179952, vol. 90, No. 23, Jun. 4, 1979.
Chemical Abstract 85:87108, vol. 85, No. 13, Sep. 27, 1976.
Chemical Abstract 77:28759, vol. 77, No. 5, Jul. 31, 1972.
Chemical Abstract 67:73724, vol. 67, No. 15, Oct. 9, 1967.
Chemical Abstract No. 54:15669c-d (1960).
Chemical Abstract No. 86:182965 (1977).
Chemical Abstract No. 82:51342 (1975).
Chemical Abstract No. 78:79575 (1973).
Kallos and Pagel, "Experimental Studies on Bronchial Asthma," Acta Medica Scandinavica, vol. 91: 292-305 (1937).
Merck Index, 11$^{th}$ Ed., Merck & Co., Nos. 242, 802-803, pp. 43, 122-123 (1989).
Larsson, Lennart, et al; The hydrogen bond condition in some anticholinergic esters of glycolic acids. I, Acta Pharm. Suecica 11, 304-308, (1974).
Nyberg, Klas, et al; Investigations of Dithienylglycolic Esters, I. Preparation of Methyl Dithienylglycoates, Magnetically Nonequivalent Protons in Dithienylglycoates; Acta Chemica Scandinavica 24 (1970) No. 5 1590-1596.
Atkinson, Edward R., et al: Parasympatholic (anticholinergic) esters of the isomeric 2-tropanols. 1. Glycolates; Journal of Medicinal Chemistry 1977, 20,(12) 1612-1617.
Archer, Sydney and Bell, Malcom ; 2α Tropanyl Acetates; Chemical Abstracts vol. 6, 1839f 1839-1840.

* cited by examiner

ANTICHOLINERGICS WHICH MAY BE USED AS MEDICAMENTS AS WELL AS PROCESSES FOR PREPARING THEM

RELATED APPLICATIONS

This application is a continuation of U.S. application Ser. No. 10/684,994, filed on Oct. 14, 2003, now abandoned, which was a continuation of U.S. application Ser. No. 09/976,950, now U.S. Pat. No. 6,706,726, for which priority is claimed, and which itself claims benefit of U.S. Provisional Application Ser. No. 60/252,777, filed on Nov. 22, 2000. Moreover, each of these applications is incorporated by reference herein.

FIELD OF THE INVENTION

The present invention relates to new anticholinergics of general formula 1

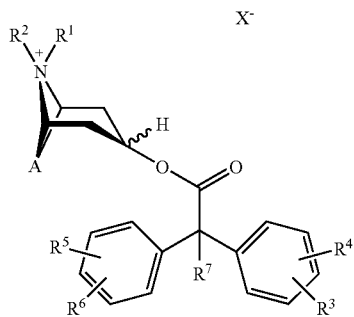

1 wherein A, $X^-$, and the groups $R^1$, $R^2$, $R^3$, $R^4$, $R^5$, $R^6$, and $R^7$ may have the meanings given in the claims and specification, processes for preparing them as well as their use as medicaments.

BACKGROUND OF THE INVENTION

Anticholinergics may be used to therapeutic effect in a wide range of illnesses. Special mention should be made, for example, of the treatment of asthma or chronic obstructive pulmonary disease (COPD). For treating these complaints, WO 92/16528 proposes anticholinergics which have a scopine, tropenol or tropine basic structure.

The underlying objective of WO 92/16528 is the preparation of anticholinergically effective compounds which are characterized by their long-lasting activity. To achieve this aim, WO 92/16528 discloses, inter alia, benzilic acid esters of scopine, tropenol, or tropine.

For treating chronic diseases, it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the wellbeing of the patient to a high degree. It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

In order to be used as a medicament taken once a day, the active substance to be given must meet particular requirements. First of all, the onset of the desired activity should take place relatively quickly after administration of the drug and ideally should have as constant an effect as possible over a subsequent fairly long period of time. On the other hand, the duration of activity of the drug should not substantially exceed a period of about one day. Ideally, an active substance has an activity profile such that the preparation of a drug for administration once a day, which contains the active substance in therapeutically beneficial doses, can be deliberately controlled.

It has been found that the benzilic acid esters of scopine, tropenol, and tropine disclosed in WO 92/16528 do not meet these stringent requirements. Because of their extremely long period of activity, which significantly exceeds the above-mentioned period of about one day, they cannot be used therapeutically for administration in a single dose per day.

The aim of the present invention is therefore to provide new anticholinergics which, by virtue of their activity profile, make it possible to prepare a drug for administration once a day. A further objective of the invention is to prepare compounds characterized by a relative rapid onset of activity. The invention further sets out to provide compounds which, after a rapid onset of activity, have as constant an activity as possible over a subsequent lengthy period of time. A further aim of the invention is to provide compounds whose duration of activity does not substantially exceed a period of about one day in therapeutically beneficial doses. Finally, the invention sets out to provide compounds which have an activity profile which ensures good control of the therapeutic effect (i.e., total therapeutic effect without side effects caused by a build-up of the substance in the body).

DETAILED DESCRIPTION OF THE INVENTION

Surprisingly, it has been found that the above objectives are achieved by means of compounds of general formula 1 wherein the group $R^7$ does not denote hydroxy.

Accordingly the present invention relates to compounds of general formula 1

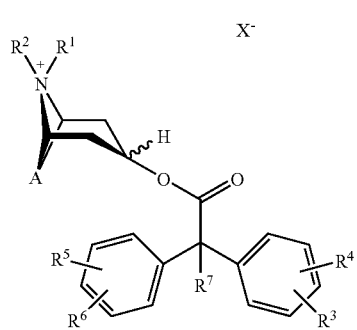

1 wherein
A denotes a double-bonded group selected from among

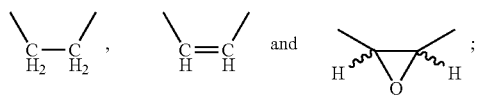

X⁻ denotes an anion with a single negative charge,

R¹ and R² denote $C_1$-$C_4$-alkyl, which may optionally be substituted by hydroxy or halogen;

R³, R⁴, R⁵, and R⁶, which may be identical or different, denote hydrogen, $C_1$-$C_4$-alkyl, $C_1$-$C_4$-alkyloxy, hydroxy, $CF_3$, CN, $NO_2$, or halogen;

R⁷ denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, $CF_3$, —$C_1$-$C_4$-alkylene-$C_1$-$C_4$-alkyloxy, —O—$COC_1$-$C_4$-alkyl, —O—$COC_1$-$C_4$-alkyl-halogen, —O—$COCF_3$, or halogen, while if A denotes

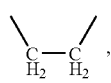

R¹ and R² denote methyl, and R³, R⁴, R⁵, and R⁶ denote hydrogen, R⁷ cannot also be hydrogen.

Preferred compounds of general formula 1 are those wherein:

A denotes a double-bonded group selected from among

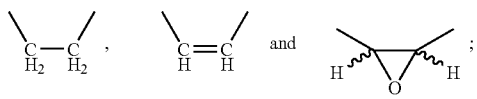

X⁻ denotes an anion with a single negative charge selected from among chloride, bromide, methylsulfate, 4-toluenesulfonate, and methanesulfonate, preferably bromide;

R¹ and R², which may be identical or different, denote a group selected from among methyl, ethyl, n-propyl and isopropyl, which may optionally be substituted by hydroxy or fluorine, preferably unsubstituted methyl;

R³, R⁴, R⁵, and R⁶, which may be identical or different, denote hydrogen, methyl, ethyl, methyloxy, ethyloxy, hydroxy, fluorine, chlorine, bromine, CN, $CF_3$, or $NO_2$; and R⁷ denotes hydrogen, methyl, ethyl, methyloxy, ethyloxy, —$CH_2$—F, —$CH_2$—$CH_2$—F, —O—$CH_2$—F, —O—$CH_2$—$CH_2$—F, —$CH_2$—OH, —$CH_2$—$CH_2$—OH, $CF_3$, —$CH_2$—OMe, —$CH_2$—$CH_2$—OMe, —$CH_2$—OEt, —$CH_2$—$CH_2$—OEt, —O—COMe, —O—COEt, —O—$COCF_3$, —O—$COCF_3$, fluorine, chlorine, or bromine.

Particularly preferred are compounds of general formula 1, wherein:

A denotes a double-bonded group selected from among:

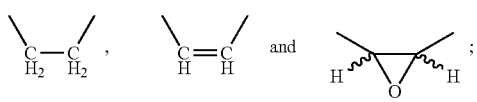

X⁻ denotes an anion with a single negative charge selected from among chloride, bromide and methanesulfonate, preferably bromide;

R¹ and R², which may be identical or different, denote a group selected from methyl and ethyl, which may optionally be substituted by hydroxy or fluorine, preferably unsubstituted methyl;

R³, R⁴, R⁵, and R⁶, which may be identical or different, denote hydrogen, methyl, ethyl, methyloxy, ethyloxy, hydroxy, fluorine, chlorine, or bromine; and R⁷ denotes hydrogen, methyl, ethyl, methyloxy, ethyloxy, $CF_3$, or fluorine.

Preferred compounds of general formula 1 according to the invention are those wherein:

A denotes a double-bonded group selected from among

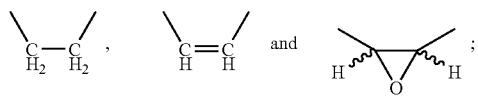

X⁻ denotes bromide;

R¹ and R², which may be identical or different, denote a group selected from methyl and ethyl, preferably methyl;

R³, R⁴, R⁵, and R⁶, which may be identical or different, denote hydrogen, methyl, methyloxy, chlorine, or fluorine; and R⁷ denotes hydrogen, methyl or fluorine.

Of particular importance according to the invention are compounds of general formula 1, wherein:

A denotes a double-bonded group selected from among

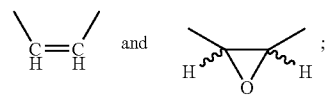

X⁻ denotes bromide;

R¹ and R² which may be identical or different denote methyl or ethyl, preferably methyl;

R³, R⁴, R⁵, and R⁶, which may be identical or different, denote hydrogen or fluorine, preferably hydrogen; and R⁷ denotes hydrogen, methyl or fluorine, preferably methyl or fluorine, most preferably methyl.

The invention relates to the compounds of formula 1, optionally in the form of the individual optical isomers, mixtures of the individual enantiomers or racemates thereof.

In the compounds of general formula 1 the groups R³, R⁴, R⁵, and R⁶, provided that they do not denote hydrogen, may each be in the ortho, meta, or para-position relative to the bond to the "—C—R⁷" group. Provided that none of the groups R³, R⁴, R⁵, and R⁶ denotes hydrogen, R³ and R⁵ are preferably linked in the para-position and R⁴ and R⁶ are preferably linked in the ortho- or meta-position, most preferably in the meta-position. If one of the groups R³ and R⁴ and one of the groups R⁵ and R⁶ denotes hydrogen, the other group in each case is preferably linked in the meta- or para-position, most preferably in the para-position. If none of the groups R³, R⁴, R⁵, and R⁶ denotes hydrogen, according to the invention the compounds of general formula 1 wherein the groups R³, R⁴, R⁵, and R⁶ have the same meaning are particularly preferred.

Of particular importance according to the invention are the compounds of general formula 1 wherein the ester-substituent on the nitrogen-bicyclic group is in the α-configuration.

These compounds correspond to general formula 1-α

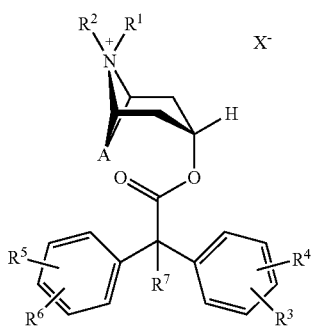

According to the invention, the following compounds are of particular importance: tropenol 2,2-diphenylpropionate-methobromide; scopine 2,2-diphenylpropionate-methobromide; scopine 2-fluoro-2,2-diphenylacetate-methobromide; and tropenol 2-fluoro-2,2-diphenylacetate-methobromide.

Unless otherwise stated, the alkyl groups are straight-chained or branched alkyl groups having 1 to 4 carbon atoms. The following are mentioned by way of example: methyl, ethyl, propyl or butyl. In some cases the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and isopropyl, butyl includes isobutyl, sec-butyl, and tert-butyl, etc.

Unless otherwise stated, the alkylene groups are branched and unbranched double-bonded alkyl bridges having 1 to 4 carbon atoms. The following are mentioned by way of example: methylene, ethylene, propylene or butylene.

Unless otherwise stated, the alkylene-halogen groups are branched and unbranched double-bonded alkyl bridges having 1 to 4 carbon atoms which are mono-, di-, or trisubstituted, preferably monosubstituted, by a halogen. Accordingly, unless otherwise stated, the alkylene-OH groups are branched and unbranched double-bonded alkyl bridges having 1 to 4 carbon atoms which are mono-, di-, or trisubstituted, preferably monosubstituted, by a hydroxy.

Unless otherwise stated, the term alkyloxy groups denotes branched and unbranched alkyl groups having 1 to 4 carbon atoms which are linked via an oxygen atom. Examples of these include: methyloxy, ethyloxy, propyloxy, or butyloxy. The abbreviations MeO-, EtO-, PropO-, or BuO- are used in some cases to denote the groups methyloxy, ethyloxy, propyloxy, or butyloxy. Unless otherwise stated, the definitions propyloxy and butyloxy include all possible isomeric forms of the groups in question. Thus, for example, propyloxy includes n-propyloxy and isopropyloxy, butyloxy includes isobutyloxy, sec-butyloxy, and tert-butyloxy, etc. In some cases, within the scope of the present invention, the term alkoxy is used instead of the term alkyloxy. Accordingly, the terms methoxy, ethoxy, propoxy, or butoxy may also be used to denote the groups methyloxy, ethyloxy, propyloxy, or butyloxy Unless otherwise stated, the term alkylene-alkyloxy groups denotes branched and unbranched double-bonded alkyl bridges having 1 to 4 carbon atoms which are mono-, di-, or trisubstituted, preferably monosubstituted, by an alkyloxy group.

Unless otherwise stated, the term —O—CO-alkyl groups denotes branched and unbranched alkyl groups having 1 to 4 carbon atoms which are linked via an ester group. The alkyl groups are linked directly to the carbonyl carbon of the ester group. The term —O—CO-alkyl-halogen group should be understood in the same way. The group —O—CO—CF$_3$ denotes trifluoroacetate.

Halogen within the scope of the present invention denotes fluorine, chlorine, bromine, or iodine. Unless stated otherwise, fluorine and bromine are the preferred halogens. The group CO denotes a carbonyl group.

The compounds according to the invention may partly be prepared, as illustrated below, analogously to procedures which are already known from the prior art (Diagram 1). The carboxylic acid derivatives of formula 3 are known in the art or may be obtained using methods of synthesis known in the art. If only suitably substituted carboxylic acids are known in the art, the compounds of formula 3 may also be obtained directly from them by acid- or base-catalyzed esterification with the corresponding alcohols or by halogenation with the corresponding halogenation reagents.

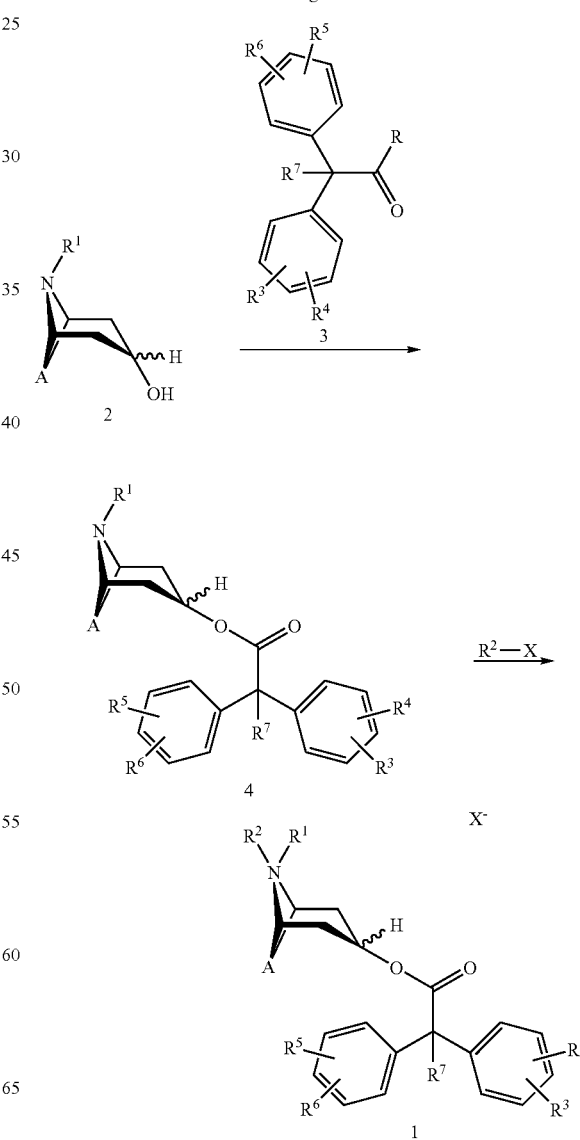

Diagram 1

Starting from the compounds of formula 2 the esters of general formula 4 may be obtained by reacting the carboxylic acid derivatives of formula 3 wherein R may denote chlorine or a $C_1$-$C_4$-alkyloxy group, for example. When R denotes $C_1$-$C_4$-alkyloxy, this reaction may be carried out, for example, in a sodium melt at elevated temperature, preferably at about 50° C.-150° C., most preferably at about 90° C.-100° C. at low pressure, preferably below 500 mbar, most preferably below 75 mbar. Alternatively, instead of the derivatives 3 wherein R denotes $C_1$-$C_4$-alkyloxy, the corresponding acid chlorides (where R is Cl) may be used.

The compounds of formula 4 thus obtained may be converted into the target compounds of formula 1 by reacting the compounds $R^2$—X, wherein $R^2$ and X may be as hereinbefore defined. This synthesis step may also be carried out analogously to the examples of synthesis disclosed in WO 92/16528.

Alternatively to the procedure illustrated in Diagram 1 for synthesizing the compounds of formula 4, the derivatives 4 in which the nitrogen bicyclic group is a scopine derivative may be obtained by oxidation (epoxidation) of compounds of formula 4 wherein the nitrogen-bicyclic group is a tropenyl group. This may be done as follows, according to the invention.

Compound 4, wherein A denotes —CH=CH—, is suspended in a polar organic solvent, preferably in a solvent selected from among N-methyl-2-pyrrolidone (NMP), dimethylacetamide, and dimethylformamide, preferably dimethylformamide, and then heated to a temperature of about 30° C. to 90° C., preferably 40° C. to 70° C. Then a suitable oxidizing agent is added and the mixture is stirred at constant temperature for 2 hours to 8 hours, preferably 3 hours to 6 hours. The preferred oxidizing agent is vanadium pentoxide mixed with $H_2O_2$, most preferably $H_2O_2$-urea complex combined with vanadium pentoxide. The mixture is worked up in the usual way. The products may be purified by crystallization or chromatography, depending on their crystallization tendencies.

Alternatively, the compounds of formula 4 wherein $R^7$ denotes halogen may also be obtained by the method shown in Diagram 2.

Diagram 2

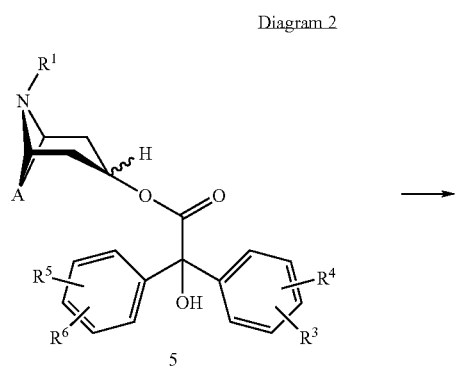

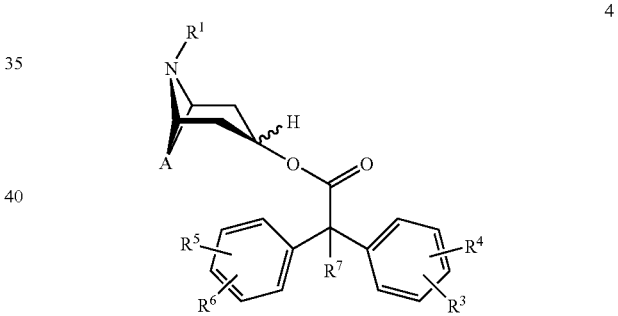

For this, the benzilic acid esters of formula 5 are converted, using suitable halogenating reagents, into the compounds 4 wherein $R^7$ denotes halogen. The reaction of halogenation to be carried out according to Diagram 2 is already sufficiently well known in the art.

The benzilic acid esters of formula 5 may be obtained in accordance with or analogously to methods known in the art (see, e.g., WO 92/16528).

As shown in Diagram 1, the intermediate products of general formula 4 are of crucial importance. Accordingly, in another aspect, the present invention relates to the intermediates of formula 4

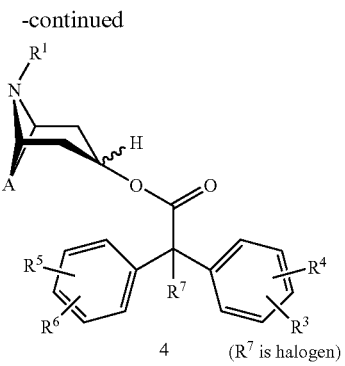

wherein:

A denotes a double-bonded group selected from among:

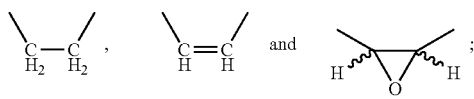

$R^1$ denotes $C_1$-$C_4$-alkyl, which may optionally be substituted by hydroxy or halogen;

$R^3$, $R^4$, $R^5$, and $R^6$, which may be identical or different, denote hydrogen, $C_1$-$C_4$-alkyl, $C_1$-$C_4$-alkyloxy, hydroxy, $CF_3$, CN, $NO_2$, or halogen;

$R^7$ denotes hydrogen, $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, $CF_3$, —$C_1$-$C_4$-alkylene-$C_1$-$C_4$-alkyloxy, —O—CO$C_1$-$C_4$-alkyl, —O—CO$C_1$-$C_4$-alkyl-halogen, —O—COCF$_3$, or halogen, while if A denotes

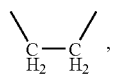

$R^1$ denotes methyl, and $R^3$, $R^4$, $R^5$, and $R^6$ denote hydrogen, $R^7$ cannot be n-propyl.

Preferred are compounds of general formula 4, wherein:

A denotes a double-bonded group selected from among:

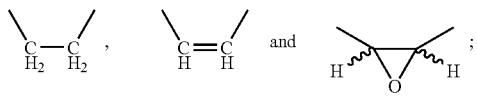

$R^1$ denotes a group selected from among methyl, ethyl, n-propyl and isopropyl, which may optionally be substituted by hydroxy or fluorine, preferably unsubstituted methyl;

$R^3$, $R^4$, $R^5$, and $R^6$, which may be identical or different, denote hydrogen, methyl, ethyl, methyloxy, ethyloxy, hydroxy, fluorine, chlorine, bromine, CN, $CF_3$, or $NO_2$; and $R^7$ denotes hydrogen, methyl, ethyl, methyloxy, ethyloxy, $-CH_2-F$, $-CH_2-CH_2-F$, $-O-CH_2-F$, $-O-CH_2-CH_2-F$, $-CH_2-OH$, $-CH_2-CH_2-OH$, $CF_3$, $-CH_2-OMe$, $-CH_2-CH_2-OMe$, $-CH_2-OEt$, $-CH_2-CH_2-OEt$, $-O-COMe$, $-O-COEt$, $-O-COCF_3$, $-O-COCF_3$, fluorine, chlorine, or bromine.

Particularly preferred are compounds of general formula 4, wherein:

A denotes a double-bonded group selected from among:

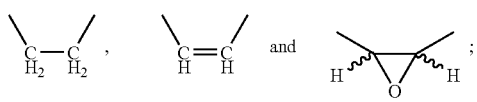

$R^1$ denotes a group selected from methyl and ethyl, which may optionally be substituted by hydroxy or fluorine, preferably unsubstituted methyl;

$R^3$, $R^4$, $R^5$, and $R^6$, which may be identical or different, denote hydrogen, methyl, ethyl, methyloxy, ethyloxy, hydroxy, fluorine, chlorine, or bromine; and $R^7$ denotes hydrogen, methyl, ethyl, methyloxy, ethyloxy, $CF_3$, or fluorine.

Preferred compounds of general formula 4 according to the invention are those wherein A denotes a double-bonded group selected from among:

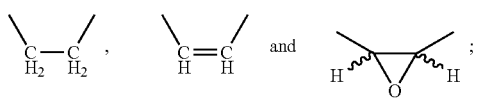

$R^1$ denotes methyl or ethyl, preferably methyl;

$R^3$, $R^4$, $R^5$, and $R^6$, which may be identical or different, denote hydrogen, methyl, methyloxy, chlorine, or fluorine; and $R^7$ denotes hydrogen, methyl, or fluorine.

Of particular importance according to the invention are compounds of general formula 4, wherein:

A denotes a double-bonded group selected from among

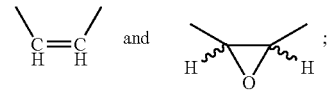

$R^1$ denotes methyl or ethyl, preferably methyl;

$R^3$, $R^4$, $R^5$, and $R^6$, which may be identical or different, denote hydrogen or fluorine, preferably hydrogen; and $R^7$ denotes hydrogen, methyl, or fluorine, preferably methyl or fluorine, most preferably methyl.

As in the compounds of general formula 1, in the intermediates of formula 4, the groups $R^3$, $R^4$, $R^5$, and $R^6$, provided that they do not denote hydrogen, may each be in the ortho, meta, or para-position relative to the bond to the "$-C-R^7$" group. Provided that none of the groups $R^3$, $R^4$, $R^5$, and $R^6$ denotes hydrogen, $R^3$ and $R^5$ are preferably linked in the para-position and $R^4$ and $R^6$ are preferably linked in the ortho- or meta-position, most preferably in the meta-position. If one of the groups $R^3$ and $R^4$ and one of the groups $R^5$ and $R^6$ denotes hydrogen, the other group in each case is preferably linked in the meta- or para-position, most preferably in the para-position. If none of the groups $R^3$, $R^4$, $R^5$, and $R^6$ denotes hydrogen, according to the invention the intermediates of general formula 1 wherein the groups $R^3$, $R^4$, $R^5$, and $R^6$ have the same meaning are particularly preferred.

The examples of synthesis described hereinafter serve to illustrate the present invention still further. However, they are intended only as examples of procedures as an illustration of the invention without restricting the invention to the subject-matter described by way of example.

EXAMPLE 1 scopine 2,2-diphenylpropionate methobromide

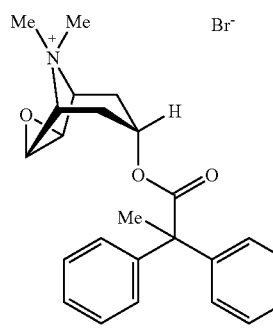

1.1.: 2,2-diphenylpropionic acid chloride 3a 52.08 g (0.33 mol) of oxalyl chloride are slowly added dropwise to a suspension of 25.0 g (0.11 mol) of 2,2-diphenylpropionic acid, 100 mL of dichloromethane, and 4 drops of dimethylformamide at 20° C. The mixture is stirred for 1 hour at 20° C. and 0.5 hours at 50° C. The solvent is distilled off and the residue remaining is used in the next step without any further purification.

1.2.: scopine 2,2-diphenylpropionate 4a

The residue obtained in step 1.1. is dissolved in 100 mL dichloromethane and at 40° C. a solution of 51.45 g (0.33 mol) of scopine in 200 mL dichloromethane is added dropwise. The resulting suspension is stirred for 24 hours at 40° C., then the precipitate formed is suction filtered and the filtrate is acidically extracted first with water, then with aqueous hydrochloric acid. The combined aqueous phases are made alkaline with aqueous sodium carbonate solution, extracted with dichloromethane, the organic phase is dried over $Na_2SO_4$, evaporated to dryness, and the hydrochloride is precipitated from the residue. The product is purified by recrystallization from acetonitrile. Yield: 20.85 g (47% of theory); TLC: $R_f$ value: 0.24 (eluent: sec-butanol/formic acid/water 75:15:10); melting point: 203° C.-204° C.

1.3: scopine 2,2-diphenylpropionate methobromide 11.98 g (0.033 mol) of 4a, 210 mL of acetonitrile, 70 mL of dichloromethane, and 20.16 g (0.1 mol) of 46.92% bromomethane in acetonitrile are combined at 20° C. and left to stand for 3 days. The solution is evaporated to dryness and the residue recrystallized from isopropanol. Yield: 11.34 g (75% of theory); melting point: 208° C.-209° C.; $C_{24}H_{28}NO_3xBr$ (458.4); elemental analysis: calculated: C, (62.89); H, (6.16); N, (3.06). found: C, (62.85); H, (6.12); N, (3.07).

EXAMPLE 2 scopine 2-fluoro-2,2-diphenylacetate methobromide

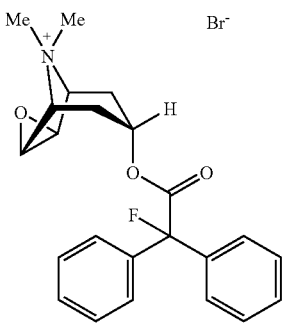

2.1: Scopine benzilate 5a

The preparation of scopine benzilate is known in the art. It is described in WO 92/16528.

2.2: scopine 2-fluoro-2,2-diphenylacetate 4b 2.66 g (0.02 mol) of dimethylaminosulfur trifluoride are cooled to 0° C. in 10 mL of dichloromethane and a solution of 5.48 g (0.015 mol) of scopine benzilate 5a in 100 mL of dichloromethane is added dropwise. Then the mixture is stirred for a further 30 minutes at 0° C. and 30 minutes at 20° C. While cooling, the solution is combined with water, $NaHCO_3$ is added (to pH 7-8), and the organic phase is separated off. The aqueous phase is extracted with dichloromethane, the combined organic phases are washed with water, dried over $Na_2SO_4$, and evaporated to dryness. The hydrochloride is precipitated from the residue and recrystallized from acetonitrile. Yield: 6.90 g (85% of theory); melting point: 227° C.-230° C.

2.3: scopine 2-fluoro-2,2-diphenylacetate methobromide 2.88 g (0.0078 mol) of the free base of scopine benzilate are reacted analogously to the procedure in step 1.3. The product is purified by recrystallization from isopropanol. Yield: 2.62 g (73% of theory); TLC: $R_f$ value: 0.31 (eluent as in step 1.2); melting point: 130° C.-134° C.

EXAMPLE 3 tropenol 2,2-diphenylpropionate methobromide

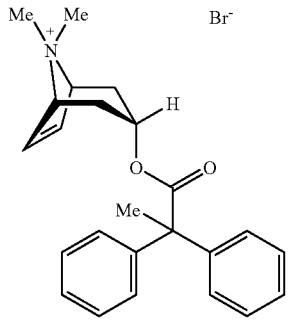

3.1.: methyl 2,2-diphenylpropionate 3b 37.60 g (0.247 mol) of DBU are added dropwise to a suspension of 50.8 g (0.225 mol) of 2,2-diphenylpropionic acid and 200 mL of acetonitrile at 20° C. 70.10 g (0.494 mol) of methyl iodide are added dropwise to the resulting solution within 30 minutes. Then the mixture is stirred overnight at 20° C. The solvent is evaporated down, the residue is extracted with diethylether/water, the organic phase is washed with water, dried over $Na_2SO_4$, and evaporated to dryness. Yield: 48.29 g of viscous residue 3.1. (89% of theory).

3.2: tropenol 2,2-diphenylpropionate 4c 4.80 g (0.02 mol) of methyl 2,2-diphenylpropionate 3b, 2.78 g (0.02 mol) of tropenol, and 0.046 g of sodium are heated as a melt at 75 mbar for 4 hours over a bath of boiling water, shaking from time to time. After cooling, the sodium residues are dissolved with acetonitrile, the solution is evaporated to dryness, and the residue extracted with dichloromethane/water. The organic phase is washed with water, dried over $MgSO_4$, and evaporated to dryness. From the residue, 4c is precipitated as the hydrochloride and this is recrystallized from acetone. Yield: 5.13 g (67% of theory); TLC: $R_f$ value: 0.28 (eluent: sec-butanol/formic acid/water 75:15:10); melting point: 134° C.-135° C.

3.3: tropenol 2,2-diphenylpropionate methobromide 2.20 g (0.006 mol) of 4c are reacted analogously to Example 1, step 1.3. The crystals formed are suction filtered, washed with dichloromethane, dried and then recrystallized from methanol/diethylether. Yield: 1.84 g (66% of theory); TLC: $R_f$ value: 0.11 (eluent as in step 1.2); melting point: 222° C.-223° C.; $C_{24}H_{28}NO_2 \times Br$ (442.4); elemental analysis: calculated: C, (65.16); H, (6.38); N, (3.17). found.: C, (65.45); H, (6.29); N, (3.16).

EXAMPLE 4 tropenol 2-fluoro-2,2-bis(3,4-difluorophenyl)acetate methobromide

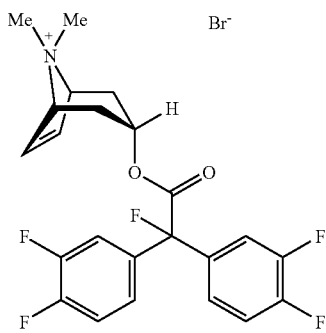

4.1.: ethyl 3,3',4,4'-tetrafluorobenzilate 3c

The Grignard reagent is prepared from 2.24 g (0.092 mol) of magnesium chips, a few granules of iodine, and 17.80 g (0.092 mol) of 1-bromo-3,4-difluorobenzene in 100 mL of THF at 50° C. After the halide has all been added, the mixture is stirred for another hour. The Grignard reagent thus obtained is added dropwise to 18.81 g (0.088 mol) of ethyl 3,4-difluorophenylglyoxylate in 80 mL of THF at 10° C.-15° C. and the mixture obtained is stirred for 2 hours at 5° C. The white suspension is poured onto ice/sulfuric acid for working up, extracted with ethyl acetate, the organic phase is washed with water, dried over $MgSO_4$, and evaporated to dryness. The crude product is purified by column chromatography (eluent: toluene). Yield: 10.80 g of oil 4.1. (38% of theory).

4.2.: tropenol 3,3',4,4'-tetrafluorobenzilate 5b 4.27 g (0.013 mol) of ethyl 3,3',4,4'-tetrafluorobenzilate 3c, 1.81 g (0.013 mol) of tropenol and 0.03 g sodium are heated as a melt at 75 mbar for 4 hours over a bath of boiling water, shaking from time to time. After cooling, the sodium residues are dissolved with acetonitrile, the solution is evaporated to dryness, and the residue extracted with dichloromethane/water. The organic phase is washed with water, dried over $MgSO_4$, and evaporated to dryness. The residue remaining is mixed with diethylether/petroleum ether (1:9), suction filtered and washed. Yield: 2.50 g (46% of theory); TLC: $R_f$ value: 0.29 (eluent: sec-butanol/formic acid/water (75:15:10)); melting point: 147° C.-148° C.

4.3: tropenol 2-fluoro-2,2-bis(3,4-difluorophenyl)acetate 4d 2.66 g (0.012 mol) of bis-(2-methoxyethyl)aminosulfur trifluoride were placed in 10 mL of dichloromethane and within 20 minutes a solution of 0.01 mol of 5b in 65 mL of dichloromethane was added dropwise at 15° C.-20° C. The mixture is stirred for 20 hours at ambient temperature, cooled to 0° C. and carefully mixed with 80 mL of water with thorough stirring. The mixture is then carefully adjusted to pH 8 with aqueous $NaHCO_3$ solution, the organic phase is separated off, the aqueous phase is extracted again with dichloromethane, the combined organic phases are washed with water, dried over $MgSO_4$, and evaporated to dryness. The hydrochloride is precipitated and recrystallized from acetonitrile/diethylether. Yield: 2.60 g of white crystals (57% of theory); melting point: 233° C.

4.4: tropenol 2-fluoro-2,2-bis(3,4-difluorophenyl)acetate methobromide 2.20 g (0.0052 mol) of 4d are reacted analogously to Example 1, step 1.3. The crystals formed are suction filtered, washed with dichloromethane, dried, and then recrystallized from methanol/diethylether. Yield: 1.95 g (72% of theory); TLC: $R_f$ value: 0.17 (eluent: n-butanol/water/formic acid (conc.)/acetone/dichloromethane (36:15:15:15:5)); melting point: 247° C.; $C_{23}H_{21}F_5NO_2 \times Br$ (518.3); elemental analysis: calculated: C, (53.30); H, (4.08); N, (2.70). found: C, (53.22); H, (4.19); N, (2.69).

EXAMPLE 5 scopine 2,2-diphenylpropionate ethylbromide

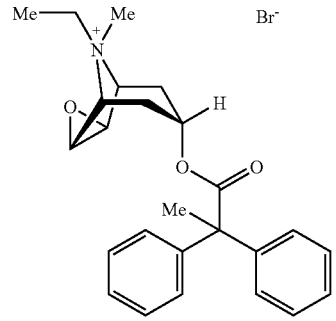

1.81 g (0.005 mol) of 4a, 35 mL of acetonitrile and 1.64 g (0.015 mol) of ethylbromide are combined at 20° C. and left to stand for 3 days. The solution is evaporated to dryness and the residue recrystallized from ethanol. Yield: 1.38 g (58% of theory); melting point: 208° C.-209° C.; TLC: $R_f$ value: 0.33 (eluent as in step 1.2); melting point: 210° C.-211° C.;

$C_{25}H_{30}NO_3xBr$ (472.42); elemental analysis: calculated: C, (63.56); H, (6.40); N, (2.96). found: C, (63.49); H, (6.24); N, (2.88).

EXAMPLE 6 scopine 2-fluoro-2,2-bis(3,4-difluorophenyl)acetate methobromide

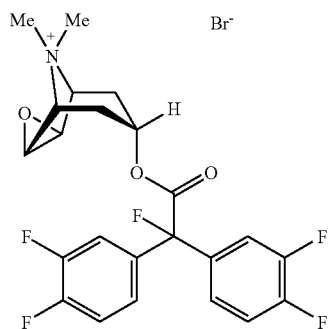

6.1.: scopine 3,3',4,4'-tetrafluorobenzilate 5c 3.61 g (0.011 mol) of ethyl 3,3',4,4'-tetrafluorobenzilate 3c, 1.71 g (0.011 mol) of scopine and 0.03 g sodium are heated as a melt at 75 mbar over a bath of boiling water for 4 hours, shaking from time to time. After cooling, the sodium residues are dissolved with acetonitrile, the solution is evaporated to dryness and the residue extracted with dichloromethane/water. The organic phase is washed with water, dried over $MgSO_4$, and evaporated to dryness. The residue remaining is combined with diethylether/petroleum ether (1:9), suction filtered and washed. Yield: 1.75 g (36% of theory); melting point: 178° C.-179° C.

6.2: scopine 2-fluoro-2,2-bis(3,4-difluorophenyl)acetate 4e 0.6 mL (0.0033 mol) of bis-(2-methoxyethyl)aminosulfur trifluoride are reacted with 1.2 g (0.0028 mol) of 5c analogously to Example 4, step 4.3. Yield: 1.15 g of colorless oil (95% of theory).

6.3: scopine 2-fluoro-2,2-bis(3,4-difluorophenyl)acetate methobromide 1.15 g (0.0026 mol) of 4e and 1.5 g (0.0079 mol) of 50% methyl bromide solution are reacted analogously to Example 1, step 1.3. The crystals formed are suction filtered, washed with dichloromethane, dried, and then recrystallized from acetone. Yield: 0.88 g (63% of theory); TLC: $R_f$ value: 0.27 (eluent: n-butanol/water/formic acid (conc.)/acetone/dichloromethane (36:15:15:15:5)); melting point: 212° C.; $C_{23}H_{21}F_5NO_3xBr$ (535.33).

EXAMPLE 7 tropenol 2-fluoro-2,2-bis(4-fluorophenyl)acetate methobromide

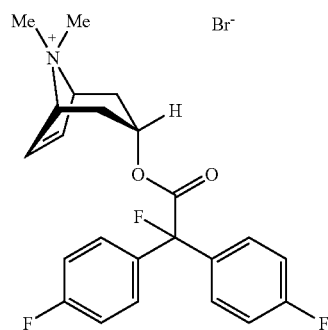

7.1.: methyl 4,4'-difluorobenzilate 3d

I.3.1.: 4,4'-difluorobenzilic acid

At about 100° C. a solution of 24.62 g (0.1 mol) of 4,4'-difluorobenzil in 250 mL of dioxane is added dropwise to a solution of 49.99 g (1.25 mol) of NaOH flakes in 300 mL of water and stirred for 2 h. The dioxane is largely distilled off and the aqueous solution remaining is extracted with dichloromethane. When the aqueous solution is acidified with sulfuric acid, a precipitate is formed which is suction filtered, washed and dried. The filtrate is extracted with dichloromethane, the organic phase is dried over $Na_2SO_4$ and evaporated to dryness. Yield: 25.01 g (95% of theory); melting point: 133° C.-136° C.

7.1.2.: methyl 4,4'-difluorobenzilate 25.0 g (0.095 mol) of 4,4'-difluorobenzilic acid are added to freshly prepared sodium ethoxide solution containing 2.17 g (0.095 mol) of sodium and 200 mL of ethanol at 20° C. and stirred for 3 h. The solution is evaporated to dryness, the residue is dissolved in DMF, 22.57 g (0.16 mol) of methyl iodide are added dropwise at 20° C. and the mixture is stirred for 24 h. It is worked up and purified analogously to compound 3b. Yield: 21.06 g of 11 (80% of theory).

7.2.: tropenol 4,4'-difluorobenzilate 5d 11.13 g (0.04 mol) of methyl 4,4'-difluorobenzilate 3d and 5.57 g (0.04 mol) of tropenol are reacted with 0.09 g sodium analogously to Example 3, step 3.2. The product is recrystallized from acetonitrile. Yield: 10.43 g (62% of theory); melting point: 233-235° C.

7.3: tropenol 2-fluoro-2,2-bis(4-fluorophenyl)acetate 4f 2.94 g (0.013 mol) of bis-(2-methoxyethyl)-aminosulfur trifluoride are reacted with 3.85 g (0.01 mol) of 5d analogously to Example 4, step 4.3 in 100 mL of dichloromethane.

The product is recrystallized from acetonitrile in the form of its hydrochloride. Yield: 2.93 g (69% of theory).

7.4: tropenol 2-fluoro-2,2-bis(4-fluorophenyl)acetate methobromide 2.6 g (0.0067 mol) of 4f and 1.9 g (0.0079 mol) of 50% methylbromide solution are reacted analogously to Example 1, step 1.3. The crystals formed are suction filtered, washed with dichloromethane, dried and then recrystallized from methanol/diethylether. Yield: 2.82 g of white crystals (87% of theory); TLC: Rf value: 0.55 (eluent: according to Example 1, step 1.2); melting point: 230-231° C.; $C_{23}H_{23}F_3NO_2xBr$ (482.34); elemental analysis: calculated: C, (57.27); H, (4.81); N, (2.90). found: C, (57.15); H, (4.84); N, (2.96).

EXAMPLE 8 scopine 2-fluoro-2,2-bis(4-fluorophenyl)acetate methobromide

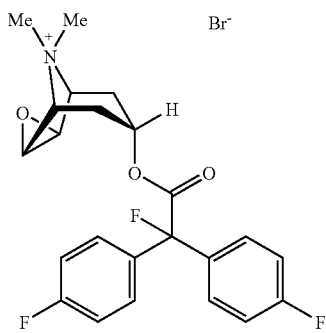

8.1: scopine 4,4'-difluorobenzilate 5e 4.22 g (0.01 mol) of tropenol 4,4'-difluorobenzilate 5d are suspended in 80 mL of DMF. At an internal temperature of about 40° C., a solution of 2.57 g (0.0273 mol) of $H_2O_2$-urea in 20 mL of water, together with 0.2 g (0.0011 mol) of vanadium (V) oxide is added and the resulting mixture is stirred for 4.5 hours at 60° C. After cooling to 20° C., the precipitate formed is suction filtered, the filtrate is adjusted to pH 3 with 4 N hydrochloric acid and combined with $Na_2S_2O_5$ dissolved in water. The resulting green solution is evaporated to dryness and the residue is extracted with dichloromethane/water. The acidic aqueous phase is made basic with $Na_2CO_3$, extracted with dichloromethane, and the organic phase is dried over $Na_2SO_4$ and concentrated. Then 0.5 mL of acetyl chloride is added at about 15° C. and stirred for 1.5 hours. After extraction with 0.1 N hydrochloric acid, the aqueous phase is made basic, extracted with dichloromethane, the organic phase is dried over $Na_2SO_4$, and evaporated to dryness. The hydrochloride is precipitated from the residue and recrystallized from methanol/diethylether. Yield: 3.61 g of white crystals (78% of theory); melting point: 243° C.-244° C.

8.2: scopine 2-fluoro-2,2-bis(4-fluorophenyl)acetate 4g 1.48 g (0.0067 mol) of bis-(2-methoxyethyl)aminosulfur trifluoride are reacted with 2.0 g (0.005 mol) of 5e analogously to Example 4, step 4.3 in 80 mL of dichloromethane. The product is recrystallized from ethanol in the form of its hydrochloride. Yield: 2.07 g (94% of theory); melting point: 238° C.-239° C.

8.3: scopine 2-fluoro-2,2-bis(4-fluorophenyl)acetate methobromide 1.6 g (0.004 mol) of 4g and 1.14 g (0.0079 mol) of 50% methylbromide solution are reacted analogously to Example 1, step 1.3. The crystals formed are suction filtered, washed with dichloromethane, dried and then recrystallized from acetonitrile. Yield: 1.65 g of white crystals (61% of theory); TLC: $R_f$ value: 0.25 (eluent: according to Example 1, step 1.2); melting point: 213° C.-214° C.; $C_{23}H_{23}F_3NO_3xBr$ (498.34); elemental analysis: calculated: C, (55.43); H, (4.65); N, (2.81). found: C, (54.46); H, (4.67); N, (2.80).

EXAMPLE 9 tropenol 2-fluoro-2,2-diphenylacetate methobromide

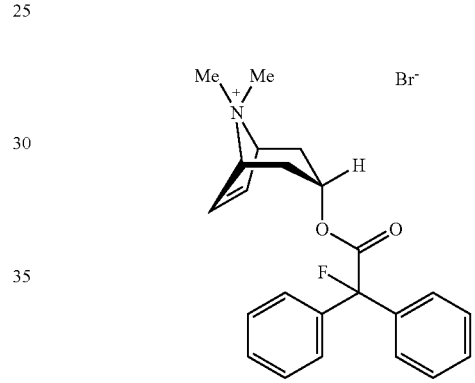

9.1.: Tropenol benzilate 5f

Tropenol benzilate and processes for preparing it are known from WO 92/16528.

9.2: tropenol 2-fluoro-2,2-diphenylacetate 4h 15.86 mL (0.086 mol) of bis-(2-methoxyethyl)aminosulfur trifluoride is reacted with 25 g (0.072 mol) of 5f analogously to Example 4, step 4.3 in 480 mL of chloroform. The product is recrystallized from acetone in the form of its hydrochloride. Yield: 18.6 g of white crystals (67% of theory); melting point: 181° C.-182° C.

9.3: tropenol 2-fluoro-2,2-diphenylacetate methobromide 11.12 g (0.032 mol) of 4h and 18.23 g (0.096 mol) of 50% methylbromide solution are reacted analogously to Example 1, step 1.3. The crystals formed are recrystallized from acetonitrile. Yield: 11.91 g of white crystals (83% of theory); TLC: $R_f$ value: 0.4 (eluent: according to Example 4, step 4.4); melting point: 238° C.-239° C.; $C_{23}H_{25}FNO_2xBr$ (446.36);

elemental analysis: calculated: C, (61.89); H, (5.65); N, (3.14). found: C, (62.04); H, (5.62); N, (3.17).

EXAMPLE 10 tropenol 2-fluoro-2,2-(3-chlorophenyl)acetate methobromide

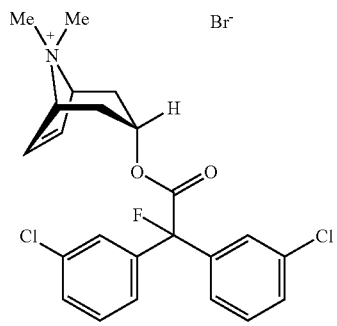

10.1.: methyl 3,3'-dichlorobenzilate 3e 10.1.1.: 3,3'-dichlorobenzil 100 mL of ethanol is used at ambient temperature and 50.0 g (0.356 mol) of 3-chlorobenzaldehyde and 4.54 g (0.018 mol) of 3-ethyl-5-(2-hydroxyethyl)-4-methylthiazolium bromide are added. Then 10.7 g (0.11 mol) of triethylamine are added dropwise. The mixture is refluxed for 3 hours and evaporated to dryness. The residue is taken up in ethyl acetate and extracted with water, sodium pyrosulfite in water, and $Na_2CO_3$ solution. After drying over $MgSO_4$, it is evaporated to dryness. The product obtained is recrystallized from isopropanol and petroleum ether. Yield: 13.2 g of white crystals (13% of theory); melting point: 69° C.-70° C.

13.0 g of the acyloin thus obtained is dissolved in 460 mL acetonitrile at room temperature (RT), 0.0867 g of vanadium (V) oxytrichloride are added and oxygen is piped in. After 1.5 hours, the solution is evaporated to dryness, extracted with ethyl acetate and water, as well as $Na_2CO_3$ solution, dried over $MgSO_4$, and evaporated to dryness. The residue remaining is stirred with petroleum ether/ethyl acetate (95:5). Yield: 12.59 g of yellow crystals (97% of theory); melting point: 116° C.-117° C.

10.1.2.: 3,3'-dichlorobenzilic acid 51.45 g (1.286 mol) of sodium hydroxide in 1000 mL water is placed in a bath of boiling water with thorough stirring and a solution of 28.5 g (0.102 mol) of 3,3'-dichlorobenzil in 700 mL dioxane is added dropwise and then stirred for another 1 hour. After cooling, the dioxane is evaporated down, the residue is diluted with water and extracted with diethylether. The organic phase is acidified, extracted with dichloromethane, dried over $MgSO_4$, and evaporated to dryness. Yield: 32.7 g (71% of theory).

10.1.3.: methyl 3,3'-dichlorobenzilate

From 100 mL of ethanol and 1.97 g (0.0855 mol) of sodium, a sodium ethoxide solution is prepared to which 26.6 g (0.0855 mol) of 3,3'-dichlorobenzilic acid in 50 mL of ethanol are added dropwise. The mixture is then stirred for 4 hours at ambient temperature. After the solvent has been distilled off, the residue is dissolved in 150 mL DMF and 24.27 g (0.171 mol) of methyl iodide are added dropwise, then stirred for another 24 hours. While cooling with ice, 300 mL of water and 200 mL of diethylether are added dropwise, the phases are separated, the aqueous phase is extracted with diethylether, then the organic phases are washed with $Na_2CO_3$ solution and shaken with water until neutral. After drying over $Na_2SO_4$, the mixture is evaporated to dryness. Yield: 22.91 g of yellow oil (82% of theory).

10.2.: tropenol 3.3'-dichlorobenzilate 5g 22.9 g (0.074 mol) of methyl 3,3'-dichlorobenzilate 3e, 15.37 g (0.11 mol) of tropenol and 0.17 g of sodium are heated for 4 hours as a melt over a bath of boiling water at 75 mbar with occasional shaking. After cooling, the sodium residues are dissolved with acetonitrile, the solution is evaporated to dryness, and the residue is extracted with dichloromethane/water. The organic phase is washed with water, dried over $MgSO_4$, and evaporated to dryness. The product is recrystallized from acetonitrile in the form of its hydrochloride. Yield: 16.83 g of white crystals (50% of theory); melting point: 184° C.-185° C.

10.3: tropenol 2-fluoro-2.2-bis(3-chlorophenyl)acetate 4i 1.48 g (0.0067 mol) of bis-(2-methoxyethyl)aminosulfur trifluoride is used in 10 mL of dichloromethane and within 20 minutes at 15° C.-20° C., a solution of 2.09 g of 5g in 65 mL of dichloromethane is added dropwise. The mixture is stirred for 20 hours at ambient temperature, cooled to 0° C., and carefully combined with 80 mL of water with thorough stirring. The mixture is then carefully adjusted to pH 8 with aqueous $NaHCO_3$ solution, the organic phase is separated off, the aqueous phase is again extracted with dichloromethane, the combined organic phases are washed with water, dried over $MgSO_4$, and evaporated to dryness. The hydrochloride is precipitated and recrystallized from acetonitrile/diethylether. Yield: 1.20 g of white crystals (53% of theory); melting point: 136° C.-137° C.

10.4: tropenol 2-fluoro-2,2-bis(3-chlorophenyl)acetate methobromide 1.0 g (0.002 mol) of 4h are reacted analogously to Example 1, step 1.3. The crystals formed are suction filtered, washed with dichloromethane, dried and then recrystallized from methanol/diethylether. Yield: 0.82 g of white crystals (80% of theory); TLC: $R_f$ value: 0.14 (eluent: n-butanol/water/formic acid(conc.)/acetone/dichloromethane (36:15:15:15:5)); melting point: 180° C.-181° C.; $C_{23}H_{23}Cl_2FNO_2 \times Br$ (515.25).

As has been found, the compounds of general formula 1 are characterized by their versatility in therapeutic use. Particular mention should be made of those applications for which the compounds of formula 1 according to the invention are preferably used on the basis of their pharmaceutical activity as anticholinergic agents. These include, for example, the treatment of asthma or chronic obstructive pulmonary disease COPD). The compounds of general formula 1 may also be used to treat vagally induced sinus bradycardia and to treat heart rhythm disorders. In general, the compounds according to the invention may also be used to treat spasms, e.g., in the gastrointestinal tract, with therapeutic benefit. They may also be used in the treatment of spasms in the urinary tract and in menstrual disorders, for example. Of the ranges of indications mentioned above, the treatment of asthma and COPD using the compounds of formula 1 according to the invention is of particular importance.

The compounds of general formula 1 may be used on their own or combined with other active substances of formula 1 according to the invention.

The compounds of general formula 1 may optionally also be combined with other pharmacologically active substances. These include, in particular, betamimetics, antiallergic agents, PAF-antagonists, leukotriene-antagonists, and corticosteroids and combinations of these active substances.

Examples of betamimetics which may be used in conjunction with the compounds of formula 1 according to the invention include compounds selected from among bambuterol, bitolterol, carbuterol, clenbuterol, fenoterol, formoterol, hexoprenaline, ibuterol, pirbuterol, procaterol, reproterol, salmeterol, sulfonterol, terbutaline, tulobuterol, 4-hydroxy-7-[2-{[2-{[3-(2-phenylethoxy)propyl]sulfonyl}ethyl] amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol, and 1-(4-ethoxycarbonylamino-3-cyano-5-fluorophenyl)-2-(tert-butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind, combined with the compounds of formula 1 according to the invention, selected from among fenoterol, formoterol, salmeterol, 1-[3-(4-methoxybenzylamino)-4-hydroxyphenyl]-2-[4-(1-benzimidazolyl)-2-methyl-2-butylamino] ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

The acid addition salts of the betamimetics selected from among the hydrochloride, hydrobromide, sulfate, phosphate, fumarate, methanesulfonate and xinafoate are preferred according to the invention. In the case of salmeterol, the salts selected from among the hydrochloride, sulfate and xinafoate are particularly preferred, especially the sulfates and xinafoates. Of outstanding importance according to the invention are salmeterol x½$H_2SO_4$ and salmeterol xinafoate. In the case of formoterol, the salts selected from among the hydrochloride, sulfate and fumarate are particularly preferred, especially the hydrochloride and fumarate. Of outstanding importance according to the invention is formoterol fumarate.

Within the scope of the present invention, the term corticosteroids, which may optionally be used in conjunction with the compounds of formula 1, denotes compounds selected from among flunisolide, beclomethasone, triamcinolone, budesonide, fluticasone, mometasone, ciclesonide, rofleponide, GW 215864, KSR 592, ST-126 and dexamethasone. The preferred corticosteroids within the scope of the present invention are those selected from among flunisolide, beclomethasone, triamcinolone, budesonide, fluticasone, mometasone, ciclesonide, and dexamethasone, while budesonide, fluticasone, mometasone, and ciclesonide, especially budesonide and fluticasone, are of particular importance. The term steroids may be used on its own, within the scope of the present patent application, instead of the term corticosteroids. Any reference to steroids within the scope of the present invention also includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. The corticosteroids may optionally also be in the form of their hydrates.

Within the scope of the present invention, the term dopamine agonists, which may optionally be used in conjunction with the compounds of formula 1, denotes compounds selected from among bromocriptine, cabergolin, alpha-dihydroergocryptine, lisuride, pergolide, pramipexol, roxindole, ropinirole, talipexole, terguride, and viozan. It is preferable within the scope of the present invention to use, as combination partners with the compounds of formula 1, dopamine agonists selected from among pramipexol, talipexole and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compounds of formula 1 include epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Preferred antiallergic agents which may be used within the scope of the present invention in combination with the compounds of formula 1 according to the invention are selected from among epinastine, cetirizine, azelastine, fexofenadine, levocabastine, loratadine, ebastine, desloratadine and mizolastine, epinastine, and desloratadine being particularly preferred. Any reference to the abovementioned antiallergic agents also includes, within the scope of the present invention, a reference to any pharmacologically acceptable acid addition salts thereof which may exist.

The following are examples of PAF antagonists which may be used in conjunction with the compounds of formula 1 according to the invention: 4-(2-chlorophenyl)-9-methyl-2-[3-(4-morpholinyl)-3-propanon-1-yl]-6H-thieno-[3,2-f][1,2,4]triazolo[4,3-a][1,4]diazepine and 6-(2-chlorophenyl)-8,9-dihydro-1-methyl-8-[(4-morpholinyl)carbonyl]-4H,7H-cyclopenta-[4,5]thieno-[3,2-f][1,2,4]triazolo[4,3-a][1,4]diazepine.

If the compounds of formula 1 are used in conjunction with other active substances, the combination with steroids or betamimetics is particularly preferred of all the categories of compounds mentioned above. Combinations with betamimetics, particularly betamimetics having a long-lasting activity, is of particular importance. The combination of the compounds of formula 1 according to the invention with salmeterol or formoterol is particularly preferred, whilst the combination with formoterol is most preferred.

Suitable preparations for administering the compounds of formula 1 include tablets, capsules, suppositories, solutions, etc. Of particular importance according to the invention (particularly when treating asthma or COPD) is the administration of the compounds according to the invention by inhalation. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates, or stabilizers such as alkali metal salts of ethylenediamine tetraacetic acid, optionally using emulsifiers and/or dispersants, whilst if water is used as the diluent, for example, optionally organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules. Suitable suppositories may be made, for example, by mixing with carriers provided for this purpose, such as neutral fats or polyethyleneglycol or the derivatives thereof. Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, and chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone) and lubricants (e.g., magnesium stearate, talc, stearic acid, and sodium lauryl sulfate).

The preparations are administered by the usual methods, preferably by inhalation in the treatment of asthma or COPD. For oral administration the tablets may, of course, contain, apart from the abovementioned carriers, additives such as sodium citrate, calcium carbonate, and dicalcium phosphate together with various additives such as starch, preferably potato starch, gelatine, and the like. Moreover, lubricants such as magnesium stearate, sodium lauryl sulfate, and talc may be used at the same time for the tabletting process. In the case of aqueous suspensions the active substances may be combined with various flavor enhancers or colorings in addition to the excipients mentioned above.

The dosage of the compounds according to the invention is naturally greatly dependent on the route of administration and the complaint to be treated. When administered by inhalation, the compounds of formula 1 are characterized by high efficacy even at doses in the µg range. The compounds of formula 1 can also be used effectively above the µg range. The dosage may then be in the gram range, for example. Particularly when administered by a method other than inhalation, the compounds according to the invention may be given in higher doses (in the range from 1 to 1000 mg, for example, although this does not imply any limitation).

The examples of formulations which follow illustrate the present invention without restricting its scope:

Examples of Pharmaceutical Formulations

A. Tablets

|  | per tablet |
|---|---|
| active substance | 100 mg |
| lactose | 140 mg |
| corn starch | 240 mg |
| polyvinylpyrrolidone | 15 mg |
| magnesium stearate | 5 mg |
|  | 500 mg |

The finely ground active substance, lactose and some of the corn starch are mixed together. The mixture is screened, then moistened with a solution of polyvinylpyrrolidone in water, kneaded, wet-granulated, and dried. The granules, the remaining corn starch and the magnesium stearate are screened and mixed together. The mixture is compressed to produce tablets of suitable shape and size.

B. Tablets

|  | per Tablet |
|---|---|
| active substance | 80 mg |
| lactose | 55 mg |
| corn starch | 190 mg |

-continued

|  | per Tablet |
| --- | --- |
| microcrystalline cellulose | 35 mg |
| polyvinylpyrrolidone | 15 mg |
| sodium-carboxymethyl starch | 23 mg |
| magnesium stearate | 2 mg |
|  | 400 mg |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

C. Ampoule Solution

| active substance | 50 mg |
| --- | --- |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

D. Metering Aerosol

| Active substance | 0.005 |
| --- | --- |
| Sorbitan trioleate | 0.1 |
| Monofluorotrichloromethane and difluorodichloromethane (2:3) | ad 100 |

The suspension is transferred into a conventional aerosol container with a metering valve. Preferably, 50 μl of suspension are delivered per spray. The active substance may also be metered in higher doses if desired (e.g., 0.02% by weight).

E. Solutions (in mg/100 mL)

| Active substance | 333.3 mg |
| --- | --- |
| Formoterol fumarate | 333.3 mg |
| Benzalkonium chloride | 10.0 mg |
| EDTA | 50.0 mg |
| HCl (1N) | ad pH 3.4 |

This solution may be prepared in the usual manner.

F. Powder for Inhalation

| Active substance | 6 μg |
| --- | --- |
| Formoterol fumarate | 6 μg |
| Lactose monohydrate | ad 25 mg |

The powder for inhalation is produced in the usual way by mixing the individual ingredients together.

G. Powder for inhalation

| Active substance | 10 μg |
| --- | --- |
| Lactose monohydrate | ad 5 mg |

The powder for inhalation is produced in the usual way by mixing the individual ingredients together.

We claim:

1. A method of treating asthma or COPD in a host in need thereof comprising administering by inhalation to the host an effective amount of a compound of formula 1

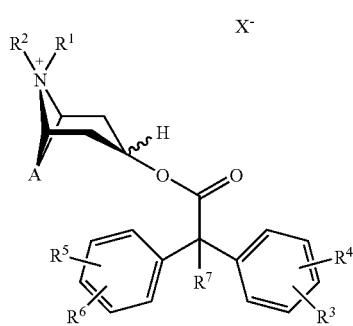

wherein:

A is a group selected from

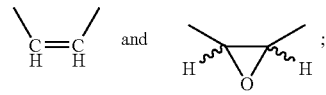

$X^-$ is an anion with a single negative charge;

$R^1$ and $R^2$, which are identical or different, are each $C_1$-$C_4$-alkyl, which are optionally substituted by hydroxy or halogen;

$R^3$, $R^4$, $R^5$, and $R^6$, which are identical or different, are each hydrogen, $C_1$-$C_4$-alkyl, $C_1$-$C_4$-alkyloxy, hydroxy, $CF_3$, CN, $NO_2$, or halogen;

$R^7$ is $C_1$-$C_4$-alkyl, $C_1$-$C_4$-alkyloxy, $C_1$-$C_4$-alkylene-halogen, halogen-$C_1$-$C_4$-alkyloxy, $C_1$-$C_4$-alkylene-OH, $CF_3$, —$C_1$-$C_4$-alkylene-$C_1$-$C_4$-alkyloxy, —O—$COC_1$-$C_4$-alkyl, —O—$COC_1$-$C_4$-alkyl-halogen, —O—$COCF_3$, or halogen.

2. The method according to claim 1, wherein in the compound of formula 1:

$X^-$ is an anion with a single negative charge selected from chloride, bromide, methylsulphate, 4-toluenesulphonate, and methanesulphonate;

$R^1$ and $R^2$, which are identical or different, are each a group selected from methyl, ethyl, n-propyl, and isopropyl, which are optionally substituted by hydroxy or fluorine;

$R^3$, $R^4$, $R^5$, and $R^6$, which are identical or different, are each hydrogen, methyl, ethyl, methyloxy, ethyloxy, hydroxy, fluorine, chlorine, bromine, CN, $CF_3$, or $NO_2$; and $R^7$ is methyl, ethyl, methyloxy, ethyloxy, —$CH_2$—F, —$CH_2$—$CH_2$—F, —O—$CH_2$—F, —O—$CH_2$—$CH_2$—F, —$CH_2$—OH, —$CH_2$—$CH_2$—OH, $CF_3$, —$CH_2$—OMe, —$CH_2$—$CH_2$—OMe, —$CH_2$—OEt, —CH$_2$—CH$_2$—OEt, —O—COMe, —O—COEt, —O—COCF$_3$, —O—COCF$_3$, fluorine, chlorine, or bromine.

3. The method according to claim 2, wherein in the compound of formula 1:
   X$^-$ is an anion with a single negative charge selected from chloride, bromide, and methanesulphonate;
   R$^1$ and R$^2$, which are identical or different, are each methyl or ethyl, which are optionally substituted by hydroxy or fluorine;
   R$^3$, R$^4$, R$^5$, and R$^6$, which are identical or different, are each hydrogen, methyl, ethyl, methyloxy, ethyloxy, hydroxy, fluorine, chlorine, or bromine; and
   R$^7$ is methyl, ethyl, methyloxy, ethyloxy, CF$_3$, or fluorine.

4. The method according to claim 3, wherein in the compound of formula 1:
   X$^-$ is bromide;
   R$^1$ and R$^2$, which are identical or different, are each methyl or ethyl;
   R$^3$, R$^4$, R$^5$, and R$^6$, which are identical or different, are each hydrogen, methyl, methyloxy, chlorine, or fluorine; and
   R$^7$ is methyl or fluorine.

5. The method according to claim 4, wherein in the compound of formula 1:
   X$^-$ is bromide;
   R$^1$ and R$^2$, which are identical or different, are each methyl or ethyl;
   R$^3$, R$^4$, R$^5$, and R$^6$, which are identical or different, denote hydrogen or fluorine; and
   R$^7$ is methyl or fluorine.

6. The method according to one of claim 1 to 5, wherein the method further comprises administering by inhalation to the host at least one additional active substance selected from the group consisting of: betamimetics, antiallergic agents, PAF-antagonists, leukotriene-antagonists, and steroids.

7. The method according to claim 1 or 5, wherein the compound of formula 1 is scopine 2,2-diphenylpropionate methobromide.

8. The method according to claim 1 or 5, wherein the compound of formula 1 is scopine 2-fluoro-2,2-diphenylacetate methobromide.

9. The method according to claim 1 or 5, wherein the compound of formula 1 is tropenol 2,2-diphenylpropionate methobromide.

10. The method according to claim 1 or 5, wherein the compound of formula 1 is tropenol 2-fluoro-2,2-bis(3,4-difluorophenyl)acetate methobromide.

11. The method according to claim 1 or 5, wherein the compound of formula 1 is scopine 2,2-diphenylpropionate ethylbromide.

12. The method according to claim 1 or 5, wherein the compound of formula 1 is scopine 2-fluoro-2,2-bis(3,4-difluorophenyl)acetate methobromide.

13. The method according to claim 1 or 5, wherein the compound of formula 1 is tropenol 2-fluoro-2,2-bis(4-fluorophenyl)acetate methobromide.

14. The method according to claim 1 or 5, wherein the compound of formula 1 is scopine 2-fluoro-2,2-bis(4-fluorophenyl)acetate methobromide.

15. The method according to claim 1 or 5, wherein the compound of formula 1 is tropenol 2-fluoro-2,2-diphenylacetate methobromide.

16. The method according to claim 1 or 5, wherein the compound of formula 1 is tropenol 2-fluoro-2,2-(3-chlorophenyl)acetate methobromide.

* * * * *